US00PP34941P2

(12) United States Plant Patent
Buchanan

(10) Patent No.: US PP34,941 P2
(45) Date of Patent: Jan. 24, 2023

(54) ***PETUNIA* PLANT NAMED 'JM09191940'**

(50) Latin Name: ***Petunia* x *hybrida***
Varietal Denomination: JM09191940

(71) Applicant: David T. Buchanan, Fredericksburg, VA (US)

(72) Inventor: David T. Buchanan, Fredericksburg, VA (US)

(73) Assignee: David T. Buchanan, Fredericksburg, VA (US)

( * ) Notice: Subject to any disclaimer, the term of this patent is extended or adjusted under 35 U.S.C. 154(b) by 0 days.

(21) Appl. No.: 17/803,590

(22) Filed: Aug. 30, 2022

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21
CPC ..... A01H 6/824; A01H 5/02
See application file for complete search history.

(56) References Cited

PUBLICATIONS

"Petunia Cold Hardiness: What Is The Cold Tolerance Of Petunias", Gardening Know How. Retrieved from URL: https://www.gardeningknowhow.com/ornamental/flowers/petunia/cold-tolerance-of-petunias.htm/?print=1&loc=top (August 5, 2022).
Alonso, Nathalie, "The Temperature Range for Petunias", SFGATE Newletters. Retrieved from URL: https://homeguides.sfgate.com/dyson-v8-worth-cost-13772127.html (May 11, 2022).
Stillman, Janice, et al., "Petunias: How to Plant, Grow, and Care for Petunias", The Old Farmer's Almanac. Retrieved from URL: https://www.almanac.com/plant/petunias (Aug. 5, 2022).

*Primary Examiner* — Keith O. Robinson
(74) *Attorney, Agent, or Firm* — Myers Bigel, P.A.

(57) ABSTRACT

'JM09191940' is a new and distinct *Petunia* cultivar having an abundance of pink flowers and the unique characteristic of a cold hardiness to temperatures as low as −10° C. (USDA Plant Hardiness Zone 8).

5 Drawing Sheets

Latin name of the genus and species: The Latin name of the novel plant cultivar disclosed herein is *Petunia* x *hybrida.*

Variety denomination: The inventive cultivar of the *Petunia* x *hybrida* disclosed herein has been given the varietal denomination 'JM09191940'.

BACKGROUND OF THE INVENTION

The present invention comprises a new and distinct cultivar of *Petunia* x *hybrida* herein referred to by the cultivar name 'JM09191940'. The USDA Plant Hardiness Zone for *Petunia* is provided as Zones 10-11 (see, Nathalie Alonso, *Home Guides,* 2022, homeguides.sfgate.com/temperature-range-petunias-65579). In an article entitled *How to Plant, Grow, and Care for Petunias,* the editors of the Almanac (almanac.com/plant/petunias) state that "[p]etunias are treated as annuals in most areas, but can be grown as tender perennials in Zones 9 to 11." Mary H. Dyer identifies the *Petunia* as an annual and states that "[a]though, *Petunias* are classified as tender perennials, they are delicate, thin-leaved tropical plants that are usually grown as annuals due to their lack of hardiness" (M. H. Dyer, *Cold Hardiness: What Is The Cold Tolerance Of Petunias* in *Gardening Know How*, 2022; gardeningknowhow.com/ornamental/flowers/petunia/cold-tolerance-of-petunias). Dyer further states that "Petunias usually tolerate temperatures as low as 39° F. (4° C.) with no problem, but they are definitely not plants that will survive the winter in most climates. *Petunias* are damaged extensively at 32° F. (0° C.) and killed very quickly by a hard freeze."

Those of us who enjoy gardening as a hobby and as a way to beautify our surroundings are always on the lookout for plants that can survive in a variety of both hot and cold environments. A new variety of cold tolerant *Petunia* was discovered growing in a rail box on the upper exposed deck of the home of the applicant/breeder in Fredericksburg, Va., having survived the winter. The plant has since survived three winters and is thriving in Fredericksburg, Va., which is in USDA Plant Hardiness Zone 7a.

The new *Petunia* cultivar was named 'JM09191940'. 'JM09191940' is a mutant or "sport" of *Petunia* plant named 'USTUNI6001' also known as 'Supertunia Vista Bubblegum' (U.S. Plant Pat. No. 17,730). In contrast to the new cultivar described herein, parent *Petunia* plant named 'USTUNI6001' is described as being hardy only in USDA Plant Hardiness Zones 10 and 11 (see, Missouri Botanical Garden, Plant Finder, *Petunia* 'USTUNI6001' Supertunia Vista Bubblegum).

'JM09191940' was first planted in the spring of 2019 and in the fall, the plant was trimmed back, with the removal of the flowering stems, but retaining the root stock. Following the winter, the root stock put out green leaves and remained in the rail box undisturbed for the 2020 growing season. 'JM09191940' flowered and thrived for a second growing season, again surviving the winter. 'USTUNI6001' *Petunia* plants were purchased and planted alongside 'JM09191940' for growing seasons 2019 and 2020, however, none of the 'USTUNI6001' *Petunia* plants survived. The new *Petunia* cultivar 'JM09191940' has survived low temperatures in the growing seasons or 2019, 2020, 2021 and 2022 as shown in Table 1.

TABLE 1

Low temperature ranges for 2019-2022 survived by 'JM09191940'

| Low temperature ranges in December 2019 | Low temperature ranges in January to March 2020 | Low temperature ranges from January-February 2021 | Low temperature ranges from January-March 2022 |
|---|---|---|---|
| −4° C. to −6° C. | −5° C. to −9° C. | 0° C.-8° C. | −7° C. to −12° C. |

As is demonstrated in Table 1, 'JM09191940' survived and grew from spring 2019 through two additional winter seasons (2019-2021) experiencing at least 160 days in temperatures from at least 0° C. to −6.5° C. range and survived at least 43 days in the temperature range between 0° C. to −6.5° C. during the winter of 2022. As shown in Table 1, 'JM09191940' survived additional days below −6.5 C.

'JM09191940' consistently survived temperatures of about −8° C. to −10° C., but in some cases, did not survive when temperatures dropped below −10° C. This indicates that 'JM09191940' is hardy to temperatures of about −10° C., but not lower temperatures. Notably, the parent *Petunia* plant, 'USTUNI6001', is described as tolerant of temperatures from 0° C. to 38° C. (U.S. Plant Pat. No. 17,730), which places it in USDA Plant Hardiness Zone 10 or 11. In contrast, the new *Petunia* cultivar 'JM09191940' can tolerate temperatures below 0° C. to at about −10 C., which makes it cold hardy to USDA Plant Hardiness Zone 8. Fredericksburg, Va., where 'JM09191940' was discovered and tested over several years, is located in USDA Plant Hardiness Zone 7a. However, the temperatures that this new *Petunia* plant survived matches best with USDA Plant Hardiness Zone 8. Similar to the parent plant, 'USTUNI6001', 'JM09191940' is heat tolerant, to about 38° C.

Asexual reproduction of 'JM09191940' is division by stem tip cuttings. The first asexual reproduction occurred in February 2021 in Fredericksburg, Va. by the process of stem tip cuttings. Six leafy rosettes of the cultivar were rooted in new containers. The parent plant and the six rooted cuttings were then used to continue the asexual reproduction by stem tip cuttings. During all asexual propagation, the characteristics of the original plant have been maintained including cold hardiness to USDA Plant Hardiness Zone 8.

SUMMARY OF THE INVENTION

'JM09191940' is a new *Petunia* cultivar that is cold hardy to USDA Plant Hardiness Zone 8, allowing it to become a part of a landscape planting that can thrive from year to year as a perennial in USDA Plant Hardiness Zones 8 and above. 'JM09191940' is a vigorous, freely branching plant with a semi-upright to cascading plant habit. The flowers of 'JM09191940' are bright pink having red-purple-colored venation.

In side-by-side comparisons conducted in Fredericksburg, Va., plants of the new cultivar 'JM09191940' differed from plants of the parent 'USTUNI6001' by its increased cold tolerance from a low temperature of about 0° C. for the parent plant to about −10° C. for 'JM09191940'.

Plants of the cultivar 'JM09191940' have not been observed under all possible environmental conditions. The phenotype may vary somewhat with variations in environment such as temperature, light intensity and daylength without, however, any variance in genotype.

BRIEF DESCRIPTION OF THE DRAWINGS

This new *Petunia* is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new *Petunia* plant.

DETAILED BOTANICAL DESCRIPTION

Figure 1:
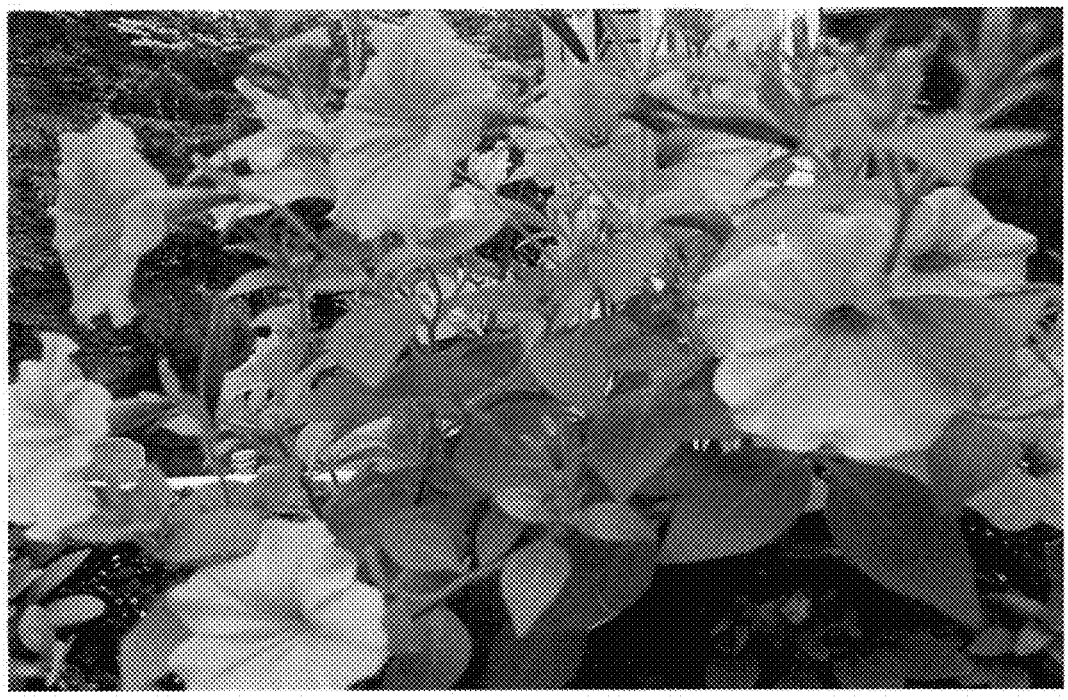
FIG. 1 is a color photograph showing the foliage and flowers of a one-year-old 'JM09191940' *Petunia* plant. Photo taken May 14, 2020, in Fredericksburg, Va.
Figure 2:
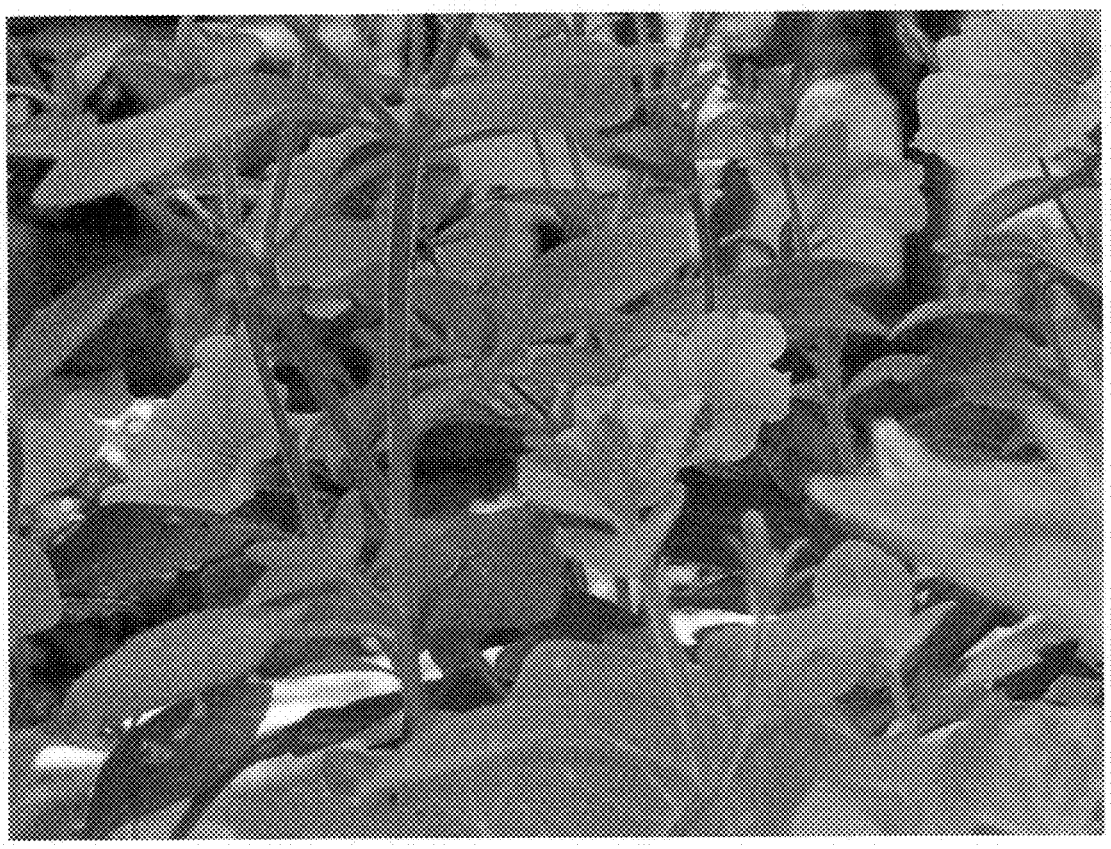
FIG. 2 is a color photograph showing the foliage and flowers of a two-year-old 'JM09191940' *Petunia* plant. Photo taken May 4, 2021, in Fredericksburg, Va.
Figure 3:
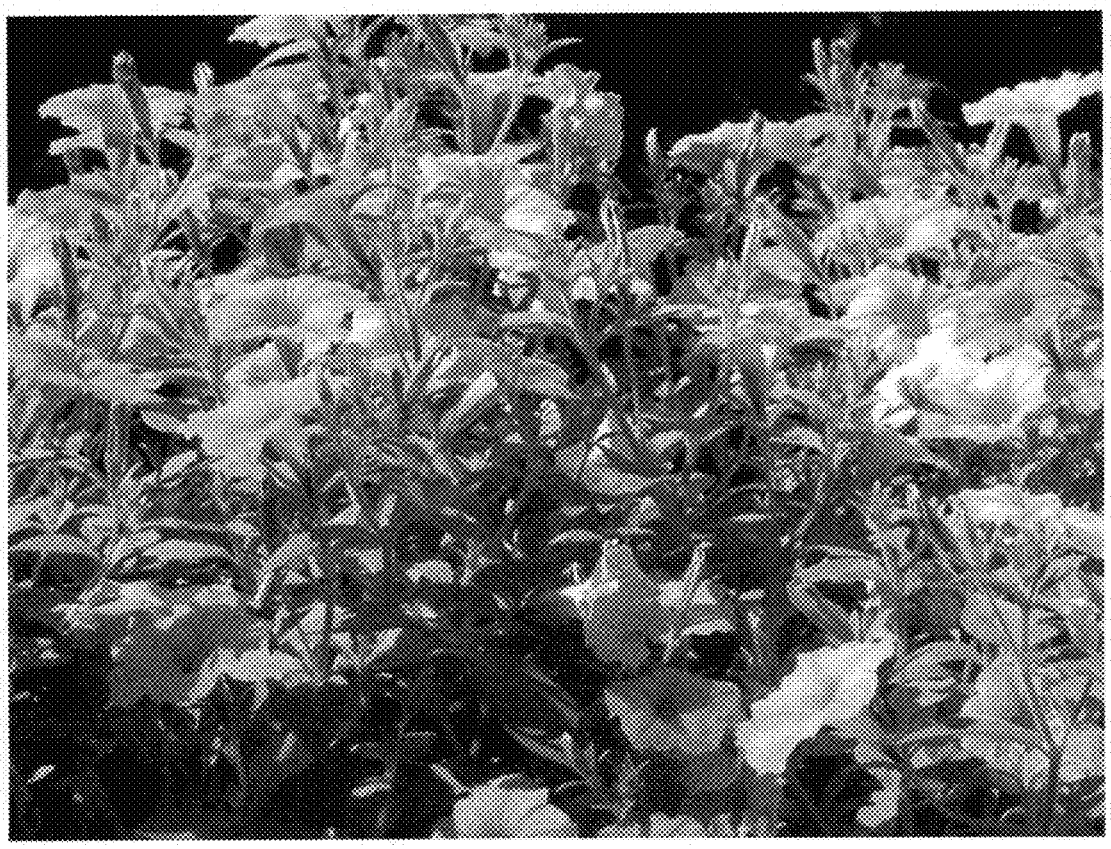
FIG. 3 is a color photograph showing the foliage and flowers of a three-year-old 'JM09191940' *Petunia* plant. Photo taken Jun. 6, 2022, in Fredericksburg, Va.
Figure 4:
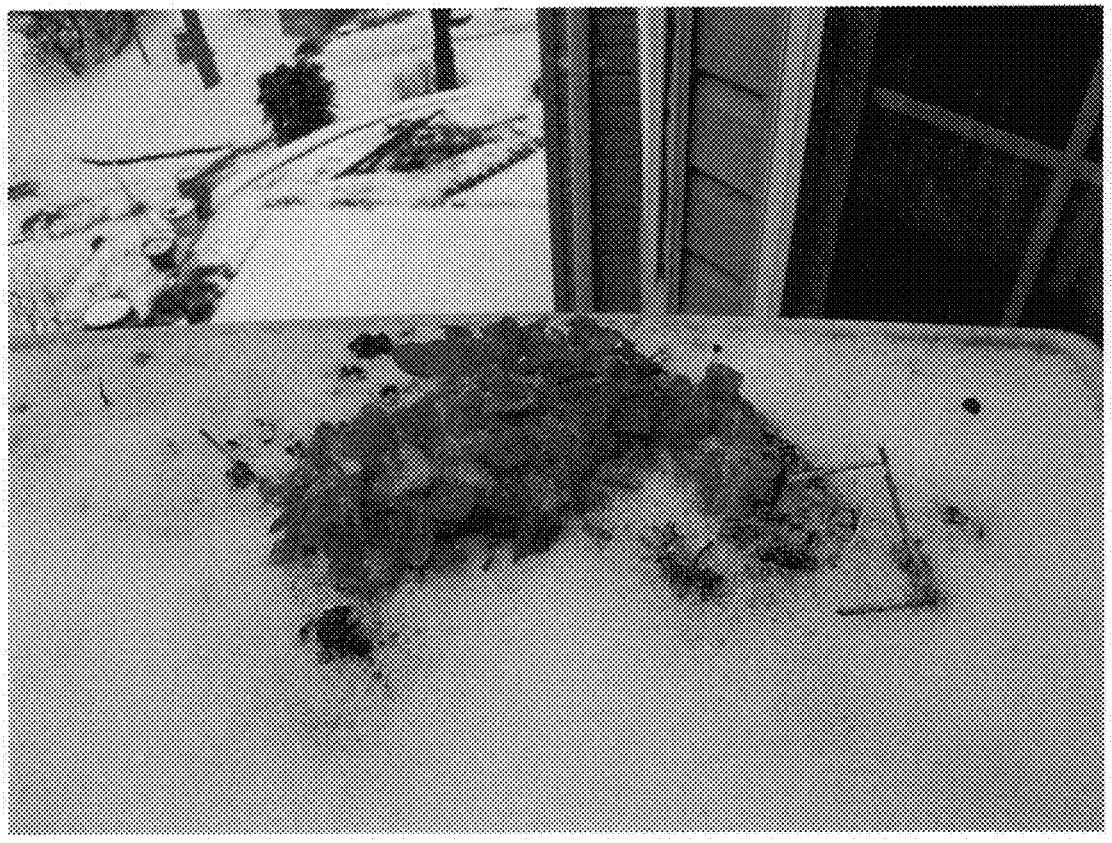
FIG. 4 is a color photograph showing the foliage of a two-year-old 'JM09191940' *Petunia* plant during the winter of 2019-2020 covered in ice and snow. Photo taken Feb. 18, 2021, in Fredericksburg, Va.
Figure 5:
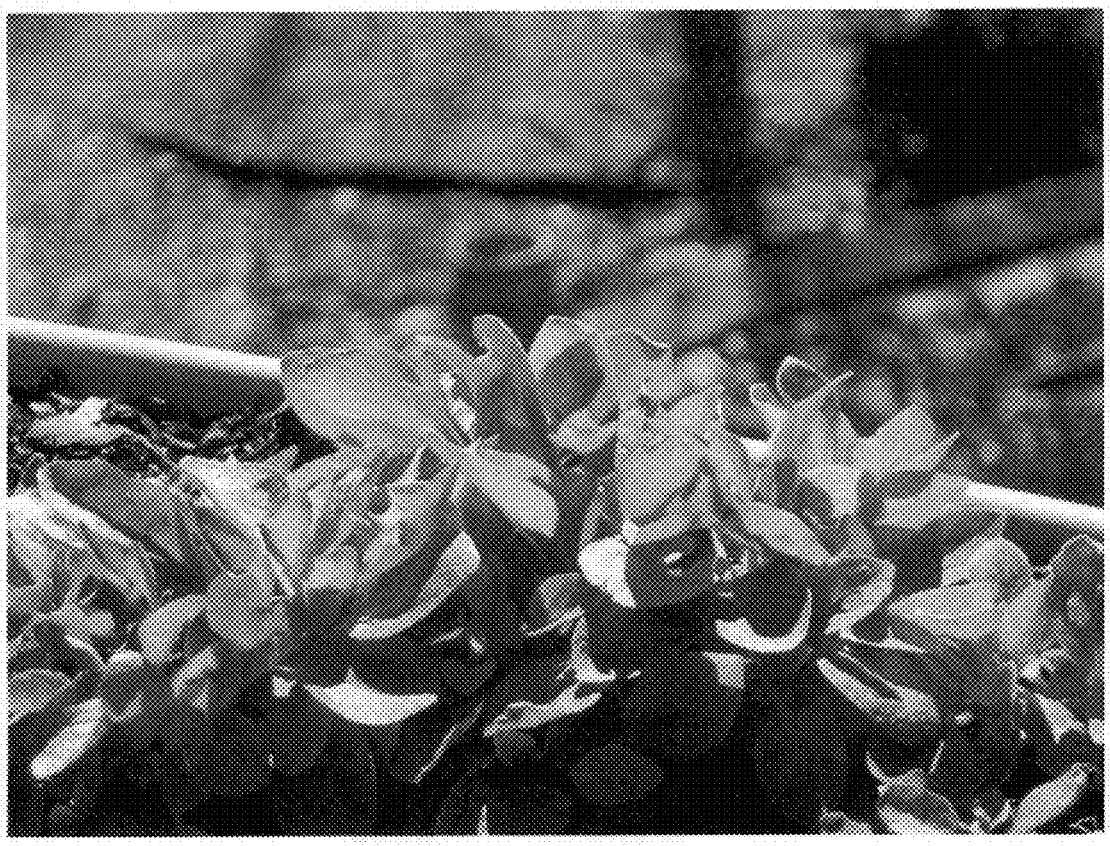
FIG. 5 is a color photograph showing the same plant in FIG. 4 after the snow and ice melted. Photo taken Feb. 23, 2021, in Fredericksburg, Va. and demonstrating the cold tolerance of the new *Petunia* variety.

The following is a detailed description of the botanical characteristics of the new and distinct variety of the *Petunia* cultivar known by the denomination 'JM09191940'. The detailed description was taken on Aug. 20, 2022, in Fredericksburg, Va. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Petunia* x *hybrida.*

*Common name.*—*Petunia.*

*Cultivar name.*—'JM09191940'.

Parentage: Sport of *Petunia* x *hybrida* cultivar 'USTUNI6001'.

Propagation: Division by stem tip cuttings

*Time to initiate roots summer and winter.*—About 15 to 20 days at 20° C.

*Time to develop roots summer and winter.*—About 15 to 20 days at 20° C.

Plant description:

*Plant form and habit.*—"JM09191940' has a very vigorous growth habit. It is an annual flowering plant in regions that have temperatures that fall below −10° C. and a perennial flowering plant in regions having temperatures of −10° C. or above (e.g., USDA Plant Hardiness Zones 8 and above). The growth of 'JM09191940' is indeterminate; initially upright then semi-upright to outwardly spreading and cascading; uniformly mounded plant form. 'JM09191940' had a freely branching habit with twelve lateral branches and numerous secondary and tertiary lateral branches on plant. Cut back enhances growth of lateral branches of 'JM09191940'.

*Height*.—From soil to top of flowers about 35 cm.

*Diameter*.—About 60 cm.

*Branching habit*.—Vigorous.

*Lateral branches*.—Average of about 12; length about 35 cm.

Foliage:

*Arrangement*.—Alternate before flowering and then opposite after flowers develop

*Number of leaves per branch*.—Average of about 14.

*Leaves*.—Simple. Leaf length: about 4 cm. Leaf width: about 2.5 cm.

*Shape*.—Ovate.

*Apex*.—Broadly acute.

*Base*.—Attenuate.

*Margin*.—Entire.

*Texture, upper and lower surfaces*.—Pubescent.

*Leaf color*.—Developing leaves, upper surface: 146A. Developing leaves, lower surface: 146B. Fully expanded leaves, upper surface: 147B. Fully expanded leaves, lower surface, 147B.

*Venation*.—Pinnate.

*Venation color*.—Upper surface: 146B. Lower surface: 146D.

*Petiole length*.—About 6 mm.

*Petiole diameter*.—About 2 mm.

*Petiole texture, upper and lower surface*.—Pubescent.

*Petiole color, upper and lower surfaces*.—146C.

Roots: Fine white, close to 155D, in color.

*Root habit*.—Freely branching.

Flowers:

*Flower type and habit*.—Single slaverform flowers; flower face upward and outward; Freely flowering habit, about 12 to 16 flower buds and open flowers per lateral branch.

*Flower size*.—Diameter: about 5 cm. Depth: about 4.5 cm. Tube length: 3.5 cm. Throat diameter, distal end: About 1 cm. Tube diameter, proximal end: about 3 mm.

*Flower buds*.—Length: about 4 cm. Diameter: about 6 mm. Shape: elongated obovate. Color 77C.

*Flower lobing*.—Medium.

*Flower venation*.—Medium.

*Petals*.—Quantity/arrangement: Five fused petals forming a funnel. Length from throat: About 2 cm. Width: About 2.2 cm. Shape: Roughly fan shaped to obovate. Apex: Broadly acute with central points. Margin: Entire; ruffled. Texture: Upper surface: Smooth, glabrous. Texture lower surface. Petal lobes: smooth, glabrous; tube pubescent. Petal Color: When opening upper surface 67C. When opening lower surface 62C. Fully opened, upper surface: 68B; toward throat and central petal lobe stripes, 68B venation, 64C; color becoming close to 69B and venation, 68A, with development. Fully opened, lower surface 65B; venation 142C. Flower throat inside 68D; venation 68B. Flower tube outside 64B; venation 146B.

*Sepals*.—

Arrangement/appearance: Single whorl of petals fused at base, star-shaped. Length: About 1 cm. Width: About 2 mm. Shape: Linear. Apex: Broadly acute. Margin: Entire. Texture: upper and lower surfaces. Pubescent. Color: upper and lower surfaces 143A.

*Peduncles*.—Length: About 4 cm. Width: About 1.5 mm. Angle: 45° to 60° from the stem. Strength: Strong. Texture: Pubescent. Color, upper and lower surfaces: 146C.

*Reproductive organs*.—Stamens: Number per flower five. Anther shape: Oval. Anther size: 1 mm×1 mm. Anther color: 196B. Pollen: Scarce. Pollen color: 198B. Pistils: Quantity per flower: one. Pistil length: About 2 cm. Style length: About 1.8 cm. Style color: 145C. Stigma shape: Rounded; anvil-shaped. Stigma color: 146B. Ovary color: 146C.

*Natural flowering season*.—Long-day response; long flowering period early spring to late frost, freeze in late autumn slows flower production; flowers continuously. Plants flower in early to mid-May from over wintering root stock. Flowers are persistent.

*Flower longevity*.—Five to seven days.

*Fragrance*.—Indistinct.

Seed/fruit production: None observed.

Disease/pest resistance: Plants of the new *Petunia* have the vigor exhibited by 'USTUNI6001'. Plants of the new *Petunia* have not been noted to be resistant to pathogens or pests common to *Petunia*.

Weather tolerance: Excellent tolerance to cold weather as well as hot weather, USDA Plant Hardiness: Zone 8.

Lasting quality of plant: Good; Blooms from early spring to late fall.

Usage: Appropriate for hanging baskets, window boxes, rail boxes patio planters and landscape use.

Garden performance: Plants of the new *Petunia* have good to excellent garden performance. Plants of the new *Petunia* are noted for drought resistance, heat tolerance and cold tolerance. This new *Petunia* performs well at temperatures between −10° C. and 38° C.

COMPARISON WITH PARENTAL PLANT

'JM09191940' differs from its parent, cultivar 'USTUNI6001', by at least having a greater cold tolerance. Specifically, 'JM09191940' is cold hardy up to USDA Plant Hardiness Zone 8, while 'USTUNI6001' is cold hardy to USDA Plant Hardiness Zone 10.

COMPARISON WITH ANOTHER *PETUNIA* VARIETY

Plants of the new *Petunia* plant named 'JM09191940' were compared to the *Petunia* variety named Supertunia® Bordeaux™ *Petunia* hybrid 'Lanbor' (U.S. Plant Pat. No. 16,144) (hereinafter 'Lanbor'). In side-by-side comparisons conducted in Fredericksburg, Va., plants of 'JM09191940' differ from the plants of 'Lanbor' in the following characteristics:

1. 'JM09191940' grows to be about 25% larger than 'Lanbor' over the same time period.
2. 'JM09191940' is more cold tolerant than 'Lanbor'.
3. 'JM09191940' has flowers that are about 3 cm larger than 'Lanbor' and the venation in the flowers is more pronounced in 'Lanbor'.

What is claimed is:

1. A new and distinct variety of *Petunia* plant named 'JM09191940' having the characteristics substantially as described and illustrated herein.

* * * * *